United States Patent
Steiner et al.

(10) Patent No.: US 8,481,929 B2
(45) Date of Patent: Jul. 9, 2013

(54) LENS FREE COLLISION CELL WITH IMPROVED EFFICIENCY

(75) Inventors: Urs Steiner, Branford, CT (US);
Felician Muntean, Danville, CA (US);
Roy P Moeller, San Leandro, CA (US);
Thinh M Ha, San Jose, CA (US)

(73) Assignee: Bruker Daltonics, Inc., Billerica, MA (US)

( * ) Notice: Subject to any disclaimer, the term of this patent is extended or adjusted under 35 U.S.C. 154(b) by 0 days.

(21) Appl. No.: 13/406,767

(22) Filed: Feb. 28, 2012

(65) Prior Publication Data
US 2013/0015349 A1 Jan. 17, 2013

Related U.S. Application Data

(60) Provisional application No. 61/508,555, filed on Jul. 15, 2011, provisional application No. 61/508,005, filed on Jul. 14, 2011.

(51) Int. Cl.
*H01J 49/06* (2006.01)
*G01N 27/00* (2006.01)
*H01J 49/00* (2006.01)
*G01N 27/62* (2006.01)

(52) U.S. Cl.
CPC ............. *H01J 49/068* (2013.01); *H01J 49/063* (2013.01); *H01J 49/066* (2013.01); *H01J 49/005* (2013.01); *G01N 27/622* (2013.01)
USPC ........... 250/292; 250/281; 250/282; 250/284; 250/286; 250/288; 250/290; 250/291; 250/294

(58) Field of Classification Search
CPC ... H01J 49/063; H01J 49/4215; H01J 49/4255; H01J 49/066; H01J 49/4225; H01J 49/004; H01J 49/0045; H01J 49/005; H01J 49/061; H01J 49/062; H01J 49/065; H01J 49/068; H01J 49/40; G01N 27/622
USPC ................. 250/281, 282, 283, 284, 288, 290, 250/291, 294, 296, 423 R, 424; 445/47
See application file for complete search history.

(56) References Cited

U.S. PATENT DOCUMENTS

| | | | | |
|---|---|---|---|---|
| 4,814,613 A | * | 3/1989 | Fite et al. | 250/292 |
| 4,963,736 A | | 10/1990 | Douglas | |
| 5,559,327 A | * | 9/1996 | Steiner | 250/292 |
| 5,652,427 A | | 7/1997 | Whitehouse | |
| 6,102,763 A | * | 8/2000 | Cueni et al. | 445/47 |
| 6,417,511 B1 | * | 7/2002 | Russ et al. | 250/292 |
| 6,576,897 B1 | * | 6/2003 | Steiner et al. | 250/292 |

(Continued)

FOREIGN PATENT DOCUMENTS

| | | |
|---|---|---|
| JP | 7073999 A | 3/1995 |
| WO | 2011081188 A1 | 7/2011 |

*Primary Examiner* — David A Vanore
(74) *Attorney, Agent, or Firm* — Robic, LLP

(57) ABSTRACT

An ion collision cell is fabricated by four semi-circular profile elements, all of which are attach to the same reference plate. Consequently, all four elements remain aligned to the same reference plate. The four elements form a semi-circular channel with a semi-circular quad electrodes. The quad electrodes receive electrical potential to form the field required to focus and maintain the ions at the center of the channel. semi-circular insulators are provided on all sides of the channel so as to seal the channel over its length from the interior of the mass spectrometer.

22 Claims, 3 Drawing Sheets

U.S. PATENT DOCUMENTS

| | | | |
|---|---|---|---|
| 6,661,001 B2 * | 12/2003 | Park | 250/287 |
| 6,797,948 B1 * | 9/2004 | Wang | 250/292 |
| 6,992,284 B2 * | 1/2006 | Schultz et al. | 250/287 |
| 7,012,250 B1 | 3/2006 | Aksyuk et al. | |
| 7,329,879 B2 * | 2/2008 | Kernan et al. | 250/396 R |
| 7,589,321 B2 * | 9/2009 | Hashimoto et al. | 250/292 |
| 7,763,849 B1 * | 7/2010 | Park | 250/291 |
| 7,923,681 B2 * | 4/2011 | Collings et al. | 250/282 |
| 8,067,747 B2 * | 11/2011 | Wollnik | 250/396 R |
| 8,222,597 B2 * | 7/2012 | Kim et al. | 250/292 |
| 8,278,618 B2 * | 10/2012 | Makarov et al. | 250/281 |
| 8,288,717 B2 * | 10/2012 | Park | 250/288 |
| 2003/0178564 A1 * | 9/2003 | Kernan et al. | 250/292 |
| 2005/0109931 A1 * | 5/2005 | Schultz et al. | 250/287 |
| 2007/0057180 A1 * | 3/2007 | Hansen et al. | 250/292 |
| 2010/0327156 A1 | 12/2010 | King | |
| 2011/0084205 A1 * | 4/2011 | Makarov et al. | 250/282 |
| 2011/0186728 A1 * | 8/2011 | Franzen et al. | 250/282 |
| 2012/0305759 A1 * | 12/2012 | Park | 250/282 |
| 2012/0326023 A1 * | 12/2012 | Kozole | 250/282 |
| 2013/0015347 A1 * | 1/2013 | Steiner | 250/288 |
| 2013/0015349 A1 * | 1/2013 | Steiner et al. | 250/288 |

* cited by examiner

*Figure 1 – Prior Art*

LENS FREE COLLISION CELL WITH IMPROVED EFFICIENCY

BACKGROUND

This application is in the field of mass spectrometers and, more specifically, to a mass analyzing spectrometer and method for fabricating a lens free collision cell. Various mass spectrometers are known in the art. An example of a prior art multi-pole mass spectrometer is illustrated in FIG. 1. For convenience of description, the mass spectrometer example of FIG. 1 is specific to a quadrupole mass analyzer, however embodiments of the invention may be used in other types of mass analyzers, e.g., a hexapole, an octapole, etc. In the mass spectrometer of FIG. 1, the sample molecules are delivered, e.g., by injector 105, into an ionization chamber 110, which ionizes the molecules, thereby acting as an ion source 110. Ions from the ion source 110 are focused and transferred to the mass analyzer 125 via ion guide or transfer optics 115, which is driven by voltage generator 120. The operation of a mass spectrometer is well understood by the skilled in the art.

An ion collision cell is incorporated in various designs of mass spectrometers, such as the triple quadrupole mass spectrometer instrument described in FIG. 3. The function of a collision cell is to modify the ions generated in the ion source, by either colliding them into fragments or to react them with other molecules. In both cases, a parent ion from the ion source is introduced into a higher-pressure region for a given time. A specifically selected gas, such as argon, nitrogen, helium, etc, is injected into the high pressure region of the collision cell, so that the ions will collide with molecules of the injected gas. The resulting fragment or product daughter ions then exit the collision cell and are analyzed by another mass analyzer and further directed to the detector.

The collision or reaction energy can be varied by the parent ion's initial velocity, the size and type of the collision gas molecules, and the number of collisions encountered. The number of collisions is depended on the gas pressure and the reaction time. If a parent ion hits a collision gas molecule, its flight path will be altered. For this reason most cell designs are built around multi-pole structures containing an ion focusing RF field.

The high pressure inside the collision cell needs to be accurately controlled, while the remaining interior of the mass spectrometer needs to be maintained in vacuum. However, gas may leak from the collision cell into the mass spectrometer through the openings for ions entering and exiting the cell. Prior art collision cells utilize seals at the entrance and exit to the cell to reduce the gas leak. However, such seals may be insufficient for high performance cell. Further information can be found in U.S. Pat. No. 6,576,897.

Accordingly, there is still a need for an improved and effective collision cell.

SUMMARY

The following summary is included in order to provide a basic understanding of some aspects and features of the disclosure. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Embodiments of the invention address the issues present in the prior art and enable simplified fabrication of a collision cell that reduces gas leakage and improves alignment of the cell's poles. According to disclosed to embodiments, the cells is formed by fours elongated semi-circle profile elements, all of which attach along their length to the same reference plate. Consequently, all four elements remain aligned to the same reference plate. The four elements form a semi-circular channel with semi-circular quad electrodes. The quad electrodes receive electrical potential to form the field required to maintain the ions at the center of the channel, i.e., at the center of the transport axis of the collision cell. Semi-circular insulators are provided on all sides of the channel so as to seal the channel over most of its length from the interior of the mass spectrometer.

BRIEF DESCRIPTION OF THE DRAWINGS

Other aspects and features of the invention would be apparent from the detailed description, which is made with reference to the following drawings. It should be appreciated that the detailed description and the drawings provides various non-limiting examples of various embodiments of the invention, which is defined by the appended claims.

DETAILED DESCRIPTION

The embodiments disclosed herein provide a collision cell for a mass analyzer. The disclosed cell is easier and cost effective to fabricate, yet maintains high alignment of the field poles, and high efficiency pressure management. The embodiments illustrated and described are for a quadrupole, but it should be appreciated that is the disclosed features are equally applicable for fabricating other multi-pole collision cells having, e.g., hexapole, octapole, etc. The collision cell constructed according to embodiments of the invention may be used in any mass spectrometer type where the ions are made to collide with gas species.

Figure 1:
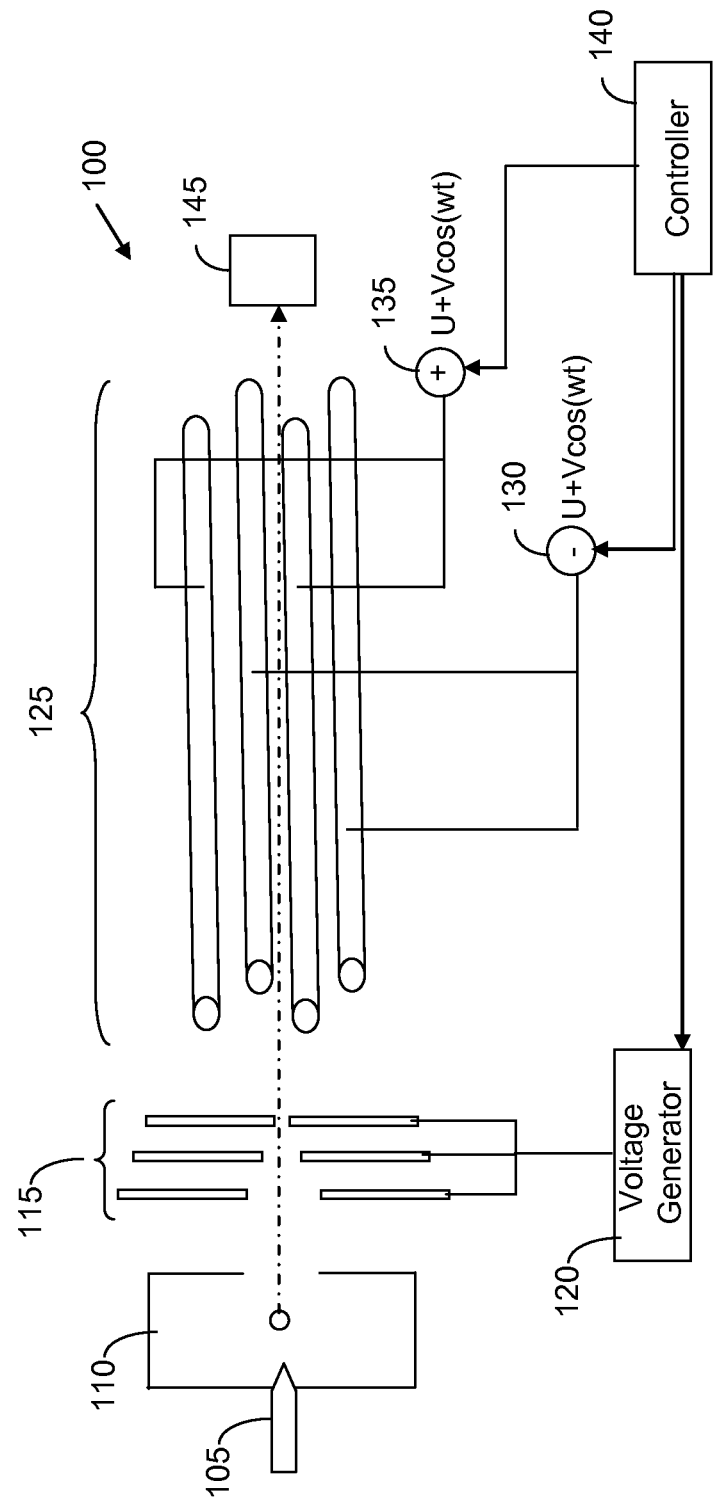
FIG. 1 is a schematic of a quadrupole mass spectrometer which may be adapted for implementing an embodiment of the invention.
Figure 2:
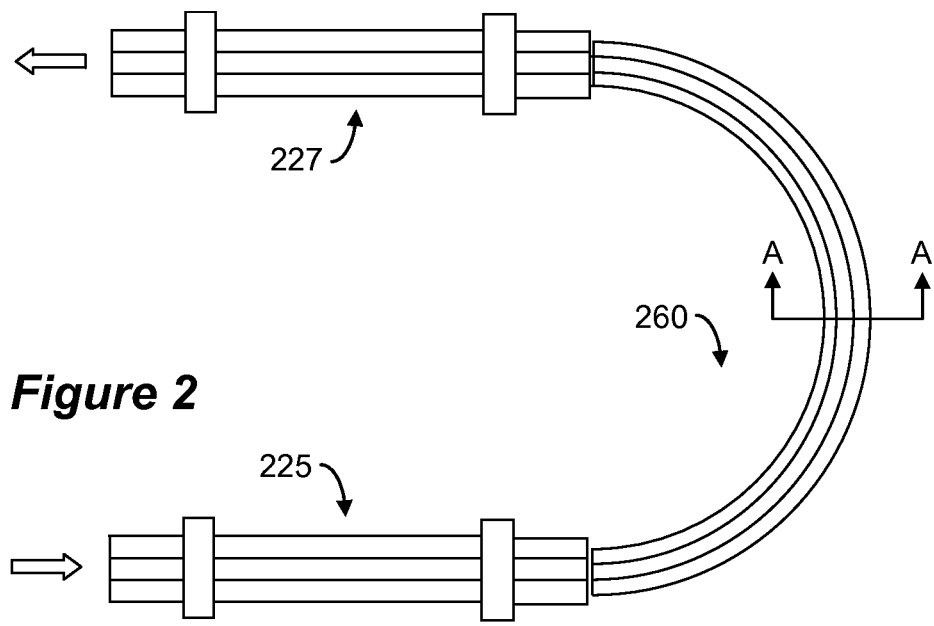
FIG. 2 is a schematic illustrating ion mass analyzer according to an embodiment of the invention.

The details of an embodiment of the invention will now be described with reference to the drawings. FIG. 2 illustrates parts of a mass spectrometer relevant to the collision cell. Various ions from the ion source enter mass analyzer 225 and are separated according to their mass to charge ratio, m/z, such that only selected ions having the filtered m/z exit the mass analyzer 225. The selected ions then enter the collision cell 260. In this embodiment, no lens is provided between the mass analyzer 225 and the collision cell 260. In the collision cell 260 the ions enter an area of injected gas at increased pressure, i.e., pressure higher than the vacuum environment prevailing inside the mass analyzer. The ions collide with the gas species and ions exit the collision cell 260 and enter the second mass analyzer 227. After exiting from the mass analyzer 227 the ions may enter a detector (not shown).

Collision cell 260 is formed of four semi-circular conductive elements that form the required field for the ion transport. The four elements are made of conductive material and are attached to a common insulating plate, so that their alignment is referenced to a single plane. This ensures accurate alignment of the poles during fabrication and at various operating temperatures.

Figure 3:
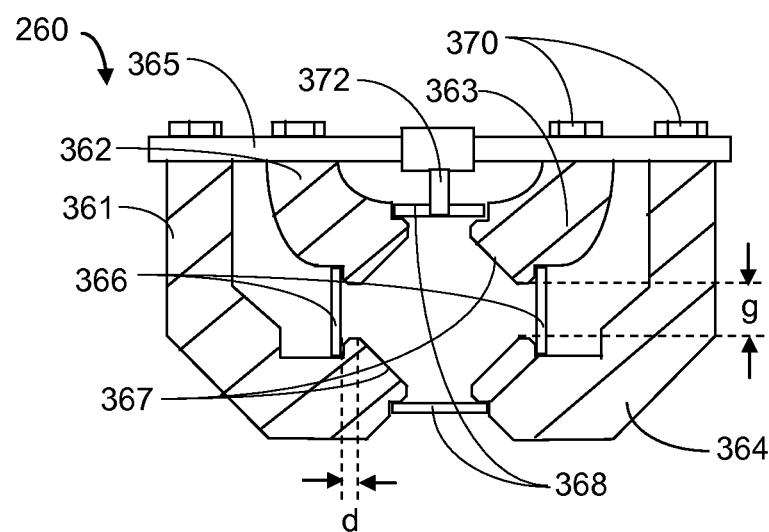
FIG. 3 is a cross-section of the collision cell shown in FIG. 2, according to embodiments of the invention.

FIG. 3 is a cross-section along the line A-A of FIG. 2. Each of the electrodes 361-364 of the quad collision cell is made of a conductive semi-circular element, having a profile that terminates to form the electrode surface 367 of the quad. All four elements 361-364 are attached along their length to insulating plate 365, as exemplified by bolts 370. In this manner, all of the quad elements have a common reference plane for the alignment of the quad electrode surfaces. This ensures proper alignment at assembly.

Additionally, in the illustrated embodiment, gas seals are provided to confine the injected gas to the volume defined by the electrodes, i.e., around the ion transport axis. As seen in the cross-section of FIG. 3, four elongated seals are provided about the quad electrodes, two vertical electrodes 366 and two horizontal electrodes 368. Together the four seals generate a seal tunnel about the axis of ion transport. In this manner, the injected gas is confined to within the tunnel of ion transport. Also, this eliminates the need for end seals, as was done in the prior art. Since the injected gas is confined to the small space within the ion transport tunnel, very little gas needs to be injected, so that the injected gas is generally confined to the area of injection and the pressure gradually lowers towards the edges of the collision cell. The gas is injected via inlet 372.

The embodiment of FIG. 3 illustrates a quad electrode arrangement, wherein each of the four elements 361-364 has a profile defining one electrode of the quad. Each electrode is separated from its neighboring electrode by a distance indicated as "g" in FIG. 3. In this embodiment, each of the four elongated seals 366 and 368 is positioned behind one of the gaps—at a distance indicated as "d", which is not larger than the gap distance g. Also, each of seals 366 and 368 is in the shape of a thin strip. Each of the thin strips is inserted between two electrodes in a perpendicular orientation. This minimizes the capacitance between each two adjacent electrodes. That is, since the seals are in the form of a thin strip oriented perpendicularly to the surface of the electrodes, it does not serve as a dielectric with respect to parasitic capacitance that may exist between the two electrodes.

Since the elongated seals are placed just behind the electrode surfaces, the injected gas is confined to the area of the quad field. Therefore, gas flow can be reduced without changing the collision rate. Consequently, gas leakage from the collision cell is minimal. Accordingly, unlike the prior art, the embodiment of FIG. 2 need not have a pre and/or post evacuation regions. That is, in the embodiment of FIG. 2, the gas is injected at the center of the semi-circular collision cell, such that the pressure at the center of the collision cell is highest and it gradually decreases towards the entrance and exit—there are no defined high and low pressure regions. On the other hand, this design enables early collision of ions with the injected gas, thereby reducing ion energy as the ions enter the collision cell. Conversely, early collisions also enhances collisional focusing, thereby reducing the ion losses in the pre-evacuation region of the prior art. Additionally, since gas flow out of the collision cell is reduced, the mass analyzers can be placed closer to the entrance and exit of the collision cell.

According to one embodiment the common plane to which all of the elements are attached to is a ceramic plate, upon which all of the electrical elements, circuitry and connections are made. In other embodiments, the plate may be a printed circuit board, upon which all of the electrical connections are made. Either arrangement eliminates all wiring for the collision cell. The electrical connections to the elements may be made using pogo pins, also eliminating wiring.

Figure 4:
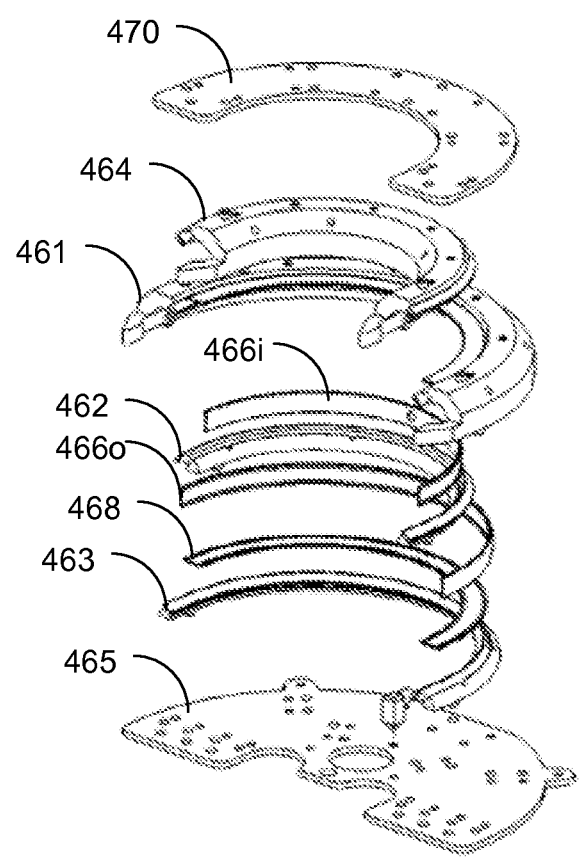
FIG. 4 is an exploded view of the collision cell shown in FIG. 2, according to embodiments of the invention.

FIG. 4 is an exploded view of the collision cell shown in FIG. 2, according to embodiments of the invention. The four poles 461-464 are connected to insulating plate 465. An inner vertical seal 466$i$ and an outer vertical seal 466$o$ are inserted together with horizontal seals 468, so as to form a seal transport tunnel around the four field generating surfaces of the poles. In this embodiment, an optional cover plate 470 is provided on top of the assembly.

The above description relates to a specific embodiment of the invention; however, the invention can be implemented using other embodiments to achieve the same improvements and features. It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

The present invention has been described in relation to particular examples, which are intended in all respects to be illustrative rather than restrictive. Those skilled in the art will appreciate that many different combinations of hardware, software, and firmware will be suitable for practicing the present invention. Moreover, other implementations of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ion collision cell, comprising:
   an insulating plate having two surfaces;
   a plurality of conductive elements, each element having a cross-section configured for forming an electrode surface;
   wherein all of the elements are attached to one surface of the insulating plate along their length, whereby the electrode surfaces of all of the elements define an ion transport tunnel.

2. The ion collision cell of claim 1, wherein the plurality of elements comprises four elements.

3. The ion collision cell of claim 1, further comprising a plurality of elongated seals provided at the periphery of the transport tunnel to thereby seal most of or the entire length of the transport tunnel.

4. The ion collision cell of claim 3, wherein the plurality of elongated seals comprise a plurality of thin flat strips.

5. The ion collision cell of claim 3, wherein each of two adjacent electrode surfaces are separated by a gap of length g, and wherein each of the elongated seals is positioned behind a corresponding gap at a distance d of length greater than length g.

6. The ion collision cell of claim 3, further comprising a gas injection inlet enabling gas injection into the ion transport tunnel.

7. The ion collision cell of claim 1, wherein the insulating plate comprises a printed circuit board.

8. The ion collision cell of claim 7, further comprising pogo pins making electrical contact to each of the elements.

9. The ion collision cell of claim 1, wherein the conductive elements are curved and form an ion transport tunnel making 180 degrees turn.

10. The ion collision cell of claim 9, wherein the plurality of elements comprises four elements and the electrode surfaces define an ion transport tunnel having a square cross-section.

11. An ion collision cell assembly, comprising:
    an insulating plate having two surfaces; and four elongated conductive elements attached to one surface of the insulating plate along their length to thereby form an ion transport tunnel, wherein each of the conductive elements is curved such that the transport tunnel forms a 180 degree turn.

12. The assembly of claim 11, wherein the ion transport tunnel has a square cross-section.

13. The assembly of claim 11, further comprising four elongated seals, each provided between two of the conductive elements, thereby sealing the transport tunnel throughout its length.

14. The assembly of claim 13, further comprising gas inlet for injecting gas into the ion transport tunnel.

15. A mass spectrometer comprising:
an ion source;
a mass analyzer having ions entering at its inlet and selected ions exiting at its outlet; and
an ion collision cell receiving the selected ions from the mass analyzer and facilitating ion collisions with gas molecules, the collision cell comprising an insulating plate with two surfaces, a plurality of conductive elements, each element having a cross-section configured for forming an electrode surface, wherein all of the conductive elements are attached to one surface of the insulating plate along their length, whereby the electrode surfaces of all of the elements define an ion transport tunnel.

16. The mass spectrometer of claim 15, wherein the plurality of elements comprises four elements.

17. The mass spectrometer of claim 15, further comprising a plurality of elongated seals provided at the periphery of the transport tunnel to thereby seal the entire length of the transport tunnel.

18. The mass spectrometer of claim 17, wherein the plurality of elongated seals comprise a plurality of thin flat strips.

19. The mass spectrometer of claim 17, wherein each of two adjacent electrode surfaces are separated by a gap of length g, and wherein each of the elongated seals is positioned behind a corresponding gap at a distance d of length greater than length g.

20. The mass spectrometer of claim 17, further comprising a gas injection inlet enabling gas injection into the ion transport tunnel.

21. A method for fabricating an ion collision cell assembly, comprising:
(a) obtaining an insulating plate having two surfaces;
(b) obtaining a plurality of elongated conductive elements, each element having a cross-section configured for forming an electrode surface; and
(c) attaching the plurality of elongated conductive elements to one surface of the insulating plate along the length of the conductive elements, such that the electrode surfaces of all of the elements define an ion transport tunnel.

22. The method of claim 21, further comprising inserting each of four elongated seals between two of the conductive elements so as to seal the transport tunnel over its length.

* * * * *